(12) United States Patent
Tsuchida et al.

(10) Patent No.: US 6,426,420 B1
(45) Date of Patent: Jul. 30, 2002

(54) PROCESS FOR PRODUCING ISOCOUMARINES AND INTERMEDIATES FOR THE SAME

(75) Inventors: Toshio Tsuchida, Yamato; Hazuki Nagai; Takashi Nakashima, both of Fujisawa; Masashi Yoshida, Chigasaki; Kaname Konuki, Yokohama; Asako Kuroda, Kawasaki; Kunio Isshiki, Zama; Tomio Takeuchi, Tokyo, all of (JP)

(73) Assignees: Mercian Corporation; Zaidan Hojin Biseibutsu Kagaku Kenkyu Kai, both of Tokyo (JP)

(*) Notice: Subject to any disclaimer, the term of this patent is extended or adjusted under 35 U.S.C. 154(b) by 0 days.

(21) Appl. No.: 09/610,362

(22) Filed: Jul. 5, 2000

(30) Foreign Application Priority Data

Jul. 22, 1999 (JP) .......................................... 11-207863
Jul. 27, 1999 (JP) .......................................... 11-212239
Nov. 25, 1999 (JP) ......................................... 11-334471
Nov. 26, 1999 (JP) ......................................... 11-336555

(51) Int. Cl.$^7$ .......................................... C07D 311/76
(52) U.S. Cl. .................................................... 549/289
(58) Field of Search ........................................ 549/289

(56) References Cited

U.S. PATENT DOCUMENTS 6,020,363 A * 2/2000 Hirano et al.

* cited by examiner

*Primary Examiner*—T. A. Solola
(74) *Attorney, Agent, or Firm*—Wenderoth, Lind & Ponack, L.L.P.

(57) ABSTRACT

Provided is a process for producing an isocoumarin-3-yl-acetic acid derivative, characterized by reacting a homophthalic acid derivative represented by a formula:

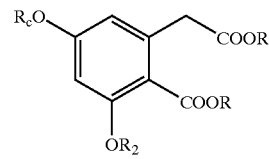

(wherein $R_c$, $R_2$ and R are mainly protecting groups) with a malonic acid derivating represented by a formula:

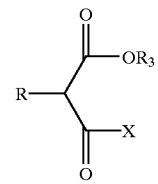

(wherein R is an organic group including a lower alkyl group; $R_3$ is a protecting group for a carboxyl group; and X is a halogen atom or a —OM group (wherein M is alkaline metal or alkaline earth metal)). According to the above process, various isocoumarin-3-yl-acetic acid derivatives can efficiently be provided.

9 Claims, No Drawings

PROCESS FOR PRODUCING ISOCOUMARINES AND INTERMEDIATES FOR THE SAME

TECHNICAL FIELD

The present invention relates to a process for producing isocoumarin-3-yl-acetic acid derivatives and to synthetic intermediates to be used in the process.

BACKGROUND ART

It is known that the isocoumarin-3-yl-acetic acid derivatives, for example, a compound represented by a formula:

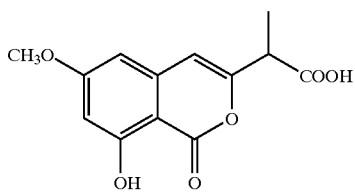

are effective for preventing and curing an abnormal immunoregulating action or a disease following angiogenesis (International Publication WO97/48693). According to this international publication pamphlet, the above compound is produced from 8-hydroxy-3-methyl-6-methoxy-isocoumarin via several steps. This is an excellent process in terms of that any of the respective steps in this process proceeds at a good yield but can not necessarily provide isocoumarin-3-yl-acetic acid derivatives having various substituents at a good efficacy.

Accordingly, there still exists a need for a process in which an isocoumarin-3-yl-acetic acid derivatives can efficiently be produced and particularly a process for producing the above derivative which can have various substituents in a 2-position of a acetic acid chain capable of exerting a strong effect on a biological activity.

DISCLOSURE OF THE INVENTION

The present inventors have found that a cyclocondensation reaction of some kind of a homophthalic acid derivative with some kind of a malonic acid derivative is allowed to proceed by one pot, whereby a wide variety of isocoumarin-3-yl-acetic acid derivatives can efficiently be produced. Further, we have found as well that in the reaction described above, a corresponding β-oxocarboxylic acid derivative before the cyclocondensation reaction can efficiently be obtained by selecting the reaction conditions. The present invention is based on such knowledge as described above.

Hence, according to the present invention, provided is the following process, that is, a process for producing isocoumarin-3-yl-acetic acid derivatives which are represented by the following formula (I):

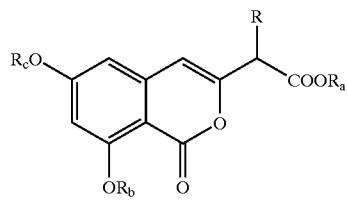

(wherein R represents a hydrogen atom, a non-substituted or substituted alkyl group, a non-substituted or substituted alkenyl group, a non-substituted or substituted alkynyl group, a non-substituted or substituted alkoxyl group, a protected amino group, a hydroxyl group or a protected hydroxyl group; $R_a$ represents a hydrogen atom or a protecting group for a carboxyl group; $R_b$ represents a hydrogen atom or a protecting group for a hydroxyl group; and $R_c$ represents a non-substituted or substituted lower alkyl group), the above process comprising:

reacting a homophthalic acid derivative represented by the following formula (III):

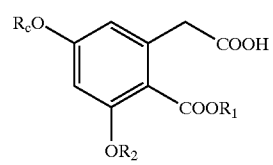

(wherein $R_c$ represents a non-substituted or substituted alkyl group; $R_1$ represents a hydrogen atom or a protecting group for a carboxyl group; and $R_2$ represents a hydrogen atom or protecting group for a hydroxyl group) with a malonic acid derivative represented by the following formula (IV):

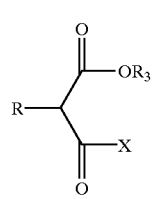

(wherein R is synonymous with that defined for formula (I); $R_3$ represents a protecting group for a carboxyl group; and X represents a —OM group (wherein M is alkaline metal or alkaline earth metal), chlorine or bromine) in an inert organic solvent in the presence of a condensing agent, wherein a β-oxocarboxylic acid derivative represented by the following formula (II) in optionally formed during the above reaction:

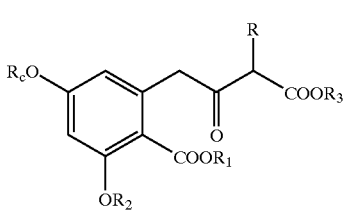

(wherein R and $R_c$ are as defined for formula (I), and $R_1$, $R_2$ and $R_3$ are as defined for formulas (III) and (IV)); and the protecting groups for a hydroxyl group and/or a carboxyl group are be subjected to an elimination reaction, if necessary.

On the other hand, both of the β-oxocarboxylic acid derivative represented by formula (II) described above and a half ester (monoester) of the homophthalic acid derivative in which $R_1$ in formulas (III) described above represents a protecting group for a carboxyl group are, to knowledge of the present inventors, novel compounds which are not described in conventional technical documents. Hence, according to the present invention, these novel compounds are provided.

BEST MODE FOR CARRYING OUT THE INVENTION

The definitions of the respective groups specifying the compounds represented by the respective formulas related to the present invention shall specifically be explained below.

The "lower alkyl group" means a linear or branched, saturated aliphatic hydrocarbon group having 1 to 6 carbon atoms and includes, for example, methyl, ethyl, n-propyl, i-propyl, n-butyl, sec-butyl, tert-butyl, n-pentyl, isoamyl and n-hexyl. The preferred alkyl group is the group having four or less carbon atoms. As described later, the examples described above can be applied in the present specification including the case where the lower alkyl group takes a share in a part of some group. Substituents in the case where these alkyl groups are substituted include halogens, a cyclo-alkyl group having 3 to 7 carbon atoms, a lower alkyl group having at least one carbon atom, an aryl group (for example, phenyl and naphthyl) which may be substituted with halogens and nitro, a lower alkoxy group, a lower alkylthio group and a mono- or di-lower alkyl-substituted amino group. At least one of these substituents can be present. Halogens mean fluorine, chlorine, bromine and iodine, but halogens in the substituents described above are preferably fluorine and chlorine. The lower alkyl groups in the lower alkoxy group, the lower alkylthio group and the lower alkyl-substituted amino group comply with the definition of the "lower alkyl group" described above (hereinafter, this is common through the whole present specification). Specific examples of the substituted alkyl group include fluoromethyl, difluoromethyl, trifluoromethyl, chloromethyl, dichloromethyl, cyclopropylmethyl, cyclopentylmethyl, 1-cyclopropylethyl, benzyl, benzhydryl, methoxymethyl, i-propoxymethyl, methylthiomethyl, methylaminomethyl, dimethylaminomethyl, dimethylaminoethyl and diethylaminomethyl.

The "lower alkenyl group" means a linear or branched aliphatic hydrocarbon group having 2 to 6 carbon atoms and a carbon-carbon double bond and includes, for example, ethenyl, propenyl, n-butenyl, i-butenyl, 3-methylbut-2-enyl and n-heptenyl. Substituents in the case where these lower alkenyl groups are substituted can be synonymous with the substituents in the "lower alkyl group" described above. Further, a substitution mode in the substituents applies correspondingly to the case of the lower alkyl group described above.

The "lower alkynyl group" means a linear or branched aliphatic hydrocarbon group having 2 to 6 carbon atoms and a carbon-carbon triple bond and includes, for example, ethynyl, propynyl, n-butynyl, i-butynyl, 3-methylbut-2-ynyl and n-pentynyl. Substituents in the case where these lower alkynyl groups are substituted can be synonymous with the substituents in the "lower alkyl group" described above. Further, a substitution mode in the substituents applies correspondingly to the case of the lower alkyl group described above.

The "lower alkoxy group" in the definition of the "R" group is common to the lower alkoxy groups given as the examples of the substituents for the lower alkyl group described above and includes, for example, methoxy, ethoxy, n-propoxy, i-propoxy, n-botoxy, sec-butoxy, tert-butoxy and n-pentyloxy. Substituents in the case where these lower alkoxy groups are substituted can be synonymous with the substituents in the "lower alkyl group" described above. Specific examples of the substituted lower alkoxy group include fluoromethoxy, difluoromethoxy, trifluoromethoxy, cyclopropylmethoxy, benzyloxy, methoxymethoxy, ethoxymethoxy, ethoxyethoxy, dimethylaminomethoxy and dimethylaminoethoxy.

A protecting group in the "protected amino group", the "protecting group for a hydroxyl group" and the "protecting group for a carboxyl group" mean groups having a function for blocking or inhibiting a reactivity of the respective corresponding functional groups in order to avoid or reduce undesirable side reactions in the reaction according to the present invention. Further, in the present invention, groups which allow the corresponding compounds to be usable as a pro-drug while these protecting groups are present can be included as well in the protecting groups. These protecting groups can be selected from those described in, for example, "Protective groups in Organic Chemistry", John Wiley and Sons, 1991, which are usually used by a person having an average skill in the art.

Among them, the protecting group in the preferred "protected amino group" includes a lower alkanoyl group (for example, acetyl, propionyl and the like), an arylcarbonyl group (for example, benzoyl and the like), a silyl group (for example, tert-butyldimethylsilyl, tert-butyldiphenylsilyl and the like), an aryl- or lower alkyl-oxy-carbonyl group (for example, benzyloxycarbonyl, tert-butoxycarbonyl and the like) and a lower alkylsulfonyl or arylsulfonyl group (for example, mesyl, tosyl and the like). The "protecting group for a hydroxyl group" includes a lower alkyl group in addition to the preceding protecting groups for an amino group.

The "protecting group for a carboxyl group" includes a lower alkyl group and a phenyl-substituted lower alkyl group which may be substituted if necessary (for example, benzyl, benzhydryl, trityl, p-nitrobenzyl and the like).

The protecting group in which the compound in the case where $R_b$ represents the protecting group for a hydroxyl group in formula (I) can be a pro-drug includes the case where $R_b$ is selected from such residues in which a hydroxyl group and a remaining carboxyl group are protected in a certain case that —$OR_b$ can finally form acetic acid ester, propionic acid ester, succinic acid ester, fumaric acid ester, maleic acid ester, lactic acid ester, tartaric acid ester or malonic acid ester.

As described above, the isocoumarin-3-yl-acetic acid derivative of formula (I) which is effective for preventing and curing an abnormal immunoregulating action or a disease following angiogenesis can advantageously be produced by a one pot reaction of the malonic acid derivative of formula (IV) with the homophthalic acid derivative of formula (III) which passes, if necessary, through the formation of the compound of formula (II) (or called a β-oxocarboxylic acid derivative) which is novel. On the other hand, according to the present invention, provided as well is a process for producing the compound of formula (I) obtained by a cyclization reaction from the compound of formula (II) which may be obtained by any production process.

Synthetic examples of the compound of formula (I) developed by the present inventors including the typical production examples of the compound of formula (III) shall specifically be explained while referring to the following scheme.

Synthetic scheme A:

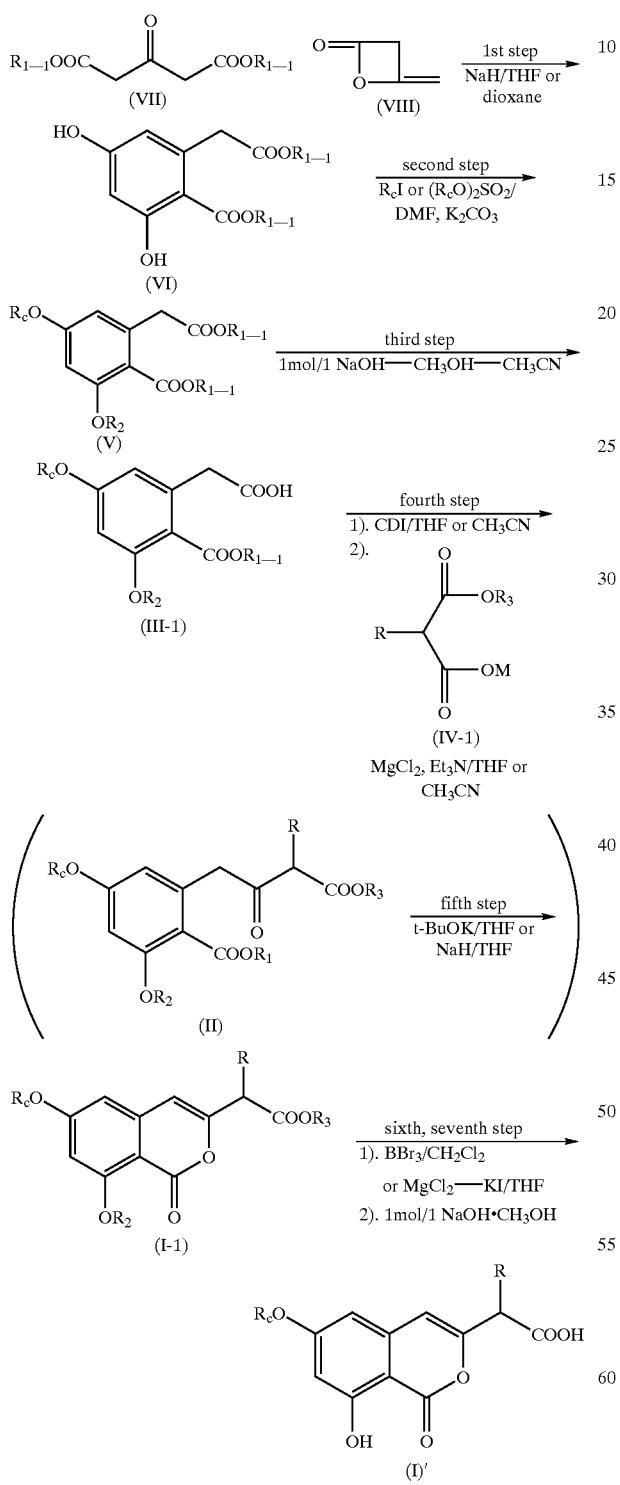

In the scheme described above, R, $R_c$, $R_1$, $R_2$, $R_3$ and M are as defined above; $R_{1\text{-}1}$ is a protecting group for a carboxyl group; THF is tetrahydrofuran; DMF is dimethylformamide; Et is ethyl; and t-Bu is tert-butyl. The fifth step shown in a branckket may be independently carried out, if necessary (hereinafter, the same shall apply).

The following 1'st step can be adopted as an alternative method for the first step described above:

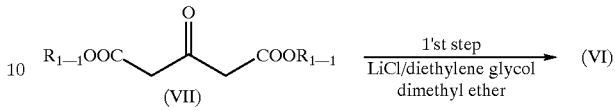

Synthetic Scheme B (Another Process for Producing the Compound in which $R_1$ of Formula (III) is a Hydrogen Atom and Using the Above Compound

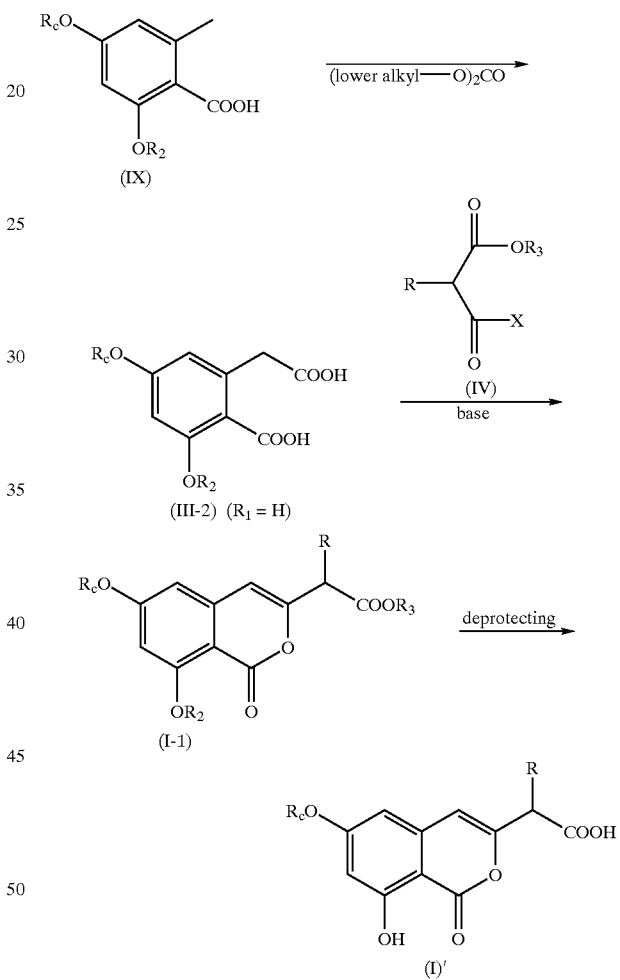

In the scheme described above, R, $R_c$, $R_2$ and $R_3$ are as defined above, and X is a —OM group (wherein M is as defined above), Cl or Br.

Explanation on Synthetic Scheme A

A part of the compounds represented by formula (VI) is publicly known according to M. Yamaguchi et. al., J. Org. Chem., 55, 1611 (1990), R. N. Hurd et. al., J. Med. Chem., 16, 543 (1973), W. R. Rough et. al., J. Org. Chem., 57, 6822 (1992) and F. M. Hauser et. al., J. Org. Chem., 42, 4155 (1977). According to M. Yamaguchi et. al., a compound in which $R_{1\text{-}1}$ in formula (VI) is tert-butyl is obtained starting from ethyl 3-hydroxyglutarate, and according to R. N. Hurd et. al, a compound in which $R_{1\text{-}1}$ in formula (VI) is methyl is obtained via a self-condensation and then the decarboxylation of a compound of formula (VII).

It is a matter of course that the compound of formula (VI) obtained by any method can be used in the preceding synthetic scheme according to the present invention, but according to the present invention, the compound of formula (VI) is preferably produced according to the 1'st step or 1'st step in the synthetic scheme described above. In this step, the intended compound of formula (VI) can be obtained by one step by reacting the acetonedicarboxylic acid ester of formula (VII) with the diketene of formula (VIII) in a suitable inert organic solvent (for example, THF, dioxane, dimethylsulfoxide (DMSO), DMF, acetonitrile and toluene) in the presence of a base, for example, sodium hydride, sodium methoxide, potassium tert-butoxide and calcium oxide. Usually, this step can be carried out by stirring a mixture of an acetonedicarboxylic acid ester and a base at 0 to 40° C. for several minutes to several ten minutes, then cooling the reaction mixture down to 10° C. or lower, adding diketene to further stir and react them at the same temperature for 0.5 to 5 hours and, if necessary, further carrying out the reaction at 20 to 70° C. A use proportion of the acetonedicarboxylic acid ester to the diketene is 1:3 to 2:1, preferably almost equimolar equivalent. A use amount of the base is a molar amount slightly exceeding that of the former.

The 1'st step is carried out in a single step by subjecting an acetonedicarboxylic acid ester represented by Formula (VII) to self condensation and decarboxylation in a suitable inert organic solvent (for example, THF, 1,4-dioxane, diethylene glycol dimethyl ether, diethylene glycol diethyl ether, diethylene glycol dibutyl ether, DMF and DMSO) in the presence of an inorganic salt (for example, alkaline metal or alkaline earth metal halides such as lithium chloride, lithium bromide, lithium iodide, lithium fluoride, sodium chloride, sodium bromide, sodium iodide, sodium fluoride, potassium chloride, potassium bromide, potassium iodide, potassium fluoride and magnesium chloride; and transition metal halides such as zinc chloride and copper chloride).

Usually, this step can be carried out by dissolving an acetonedicarboxylic acid ester in an organic solvent, adding an alkaline metal salt and stirring and reacting at 50 to 150° C. (preferably about 130° C.) for 1 to 30 hours (preferably about 3 to 23 hours). Provided that when THF or 1,4-dioxane is used as the solvent, the reaction is carried out on a refluxing condition.

A use proportion of the acetonedicarboxylic acid ester to the alkaline metal salt is 1:0.1 to 0.1:1, preferably 1:0.1 to 1:1.5.

The production process for the compound of Formula (VI) shown in the 1st step and the 1'st step was described in a conventional technical literature as long as the present inventors investigated.

The compound of formula (VI) thus formed can be obtained by refining the reaction mixture of the compound of formula (VI) thus formed by extraction with an organic solvent such as ethyl acetate and, if necessary, chromatography using silica gel.

The compound of formula (V) having a form in which the hydroxyl group of the compound of formula (VI) is protected in the second step is partially publicly known as well according to M. Yamaguchi et. al. Hydroxyl groups in a 2-position and a 4-position of the compound of formula (VI) are etherified at the same time or in order one after the other, or the hydroxyl group in the 4-position is etherified and then the hydroxyl group in the 2-position is esterified, or etherification and esterification can be carried out in a reverse order. These etherification and esterification can be carried out using suitable reactants corresponding to $R_c$ and $R_2$ according to publicly known methods.

Further, the compound of Formula (V) can be obtained as well by esterifying two carboxyl groups of the compound of Formula (III-2) which shall be described later.

The compound of formula (V) thus obtained is subjected to a partial hydrolytic reaction of a homophthalic acid diester in the third step and converted into a half-ester (or a homophthalic acid monoester) of formula (III-1) in which an acetic acid ester part (an alkylcarboxylic acid ester group) is hydrolyzed into a free carboxyl group. Even when two $R_{1-1}$'s in the compound of formula (V) are the same group, the partial hydrolysis described above goes on efficiently, but respective $R_{1-1}$'s can be selected as well so that the alkyl carboxylic acid ester group is hydrolyzed more easily than the aryl carboxylic acid ester group. A combination thereof includes, for example, a case where $R_{1-1}$ in the former is methyl, ethyl, propyl or isopropyl and $R_{1-1}$ in the latter is benzyl. This hydrolytic reaction condition is under the control of the kind of $R_{1-1}$ selected, and the hydrolysis is preferably carried out usually in a water base solution in the presence of a base (for example, NaOH, KOH, $Ba(OH)_2$ and LiOH).

The half-ester of formula (III-1) can be refined by extraction with an organic solvent and, if necessary, chromatography using silica gel. The half-ester (or homophthalic acid monoester) of formula (111-1) is not described as well in conventional technical documents.

In the fourth step, the homophthalic acid monoester described above is reacted with the malonic acid derivative of formula (IV-1) in an inert organic solvent. Any solvents can be used as long as they do not exert an adverse effect on the present reaction. Usually, THF, DMF, dioxane or acetonitrile is preferably used. The malonic acid monoester salt of formula (IV-1) (M in formula (IV-1) is an alkaline metal such as potassium and sodium or an alkaline earth metal such as calcium and magnesium) is stirred in a solvent at 0 to 40° C., suitably a room temperature (usually 20 to 30° C.) for 0.5 to 5 hours in the presence of a condensing agent, particularly a base (for example, trtiethylamine, diisopropylamine, pyridine and lutidine) and an additive (for example, $MgCl_2$, $MgBR_2$, Mg and MgO) to prepare a reaction solution. Separately, the compound of formula (III-1) is stirred preferably in the solvent used for preparing the reaction solution described above at 0 to 40° C., suitably a room temperature for 0.5 to 5 hours in the coexistence of a condensing agent (for example, carbonyldiimidazole and the like) to prepare another reaction solution. Both reaction solutions thus prepared are mixed at 0 to 40° C. and then, if necessary, heated while stirring. The stirring time can be determined by tracing a consumed level of the starting material and/or a kind or a level of a newly resulting product on a thin layer chromatogram. Usually, it is about 4 to 20 hours in stirring at a room or elevated temperature. Thus, the compound of formula (I-1) can be produced by one pot, but the compound of formula (II) formed in the middle of the reaction may be separated from the reaction mixture to carry out separately a cyclization reaction to thereby produce the compound of formula (I-1).

The compound of formula (IV-1) used for the raw material is a compound which is almost publicly known in documents, and a novel compound can be produced in the same manner as in known compounds or from known compounds.

In the reaction described above, the compound of formula (III-1) and the compound of formula (IV-1) are used usually in a proportion of 1:1 molar equivalent to 1:4 molar equivalent. The optimum concentrations of these compounds in the reaction solution can be determined by a person having an average skill in the art by carrying out simple experiments.

The cyclization reaction of the compound of formula (II) can be carried out by stirring the reaction solution in a suitable inert organic solvent (for example, THF, DMF, dimethoxyethane, dioxane, acetonitrile and toluene) at 0 to 40° C., suitably a room temperature in the presence of a base (for example, amines such as triethylamine, diisopropylamine, pyridine and lutidine, or alkaline metal alcoholate such as potassium t-butoxide and sodium methoxide or sodium hydride). This reaction causes an elimination of $R_2$ and $R_3$ in a certain case in addition to the cyclization described above. Thus, the compound of formula (I-1) or (I)' can be obtained.

When the mixture of the preparation of the compound of formula (IV-1) described above and the preparation of the compound of formula (III-1) is reacted by one pot, the reaction is carried out preferably by stirring the mixture for a fixed time and the further elevating the temperature. In this case, the fixed time described above is decided by analyzing an aliquot of the reaction solution with the passage of time by means of a thin layer chromatography to determine the extent of a dissipation in spots which are considered to correspond to the compound of formula (II). The reaction solution is heated after the compound of formula (II) of exceeding almost 50%, preferably almost 80% or more in terms of the extent of dissipation is consumed. The temperature can be elevated up to the boiling point of the solvent used.

In this one pot reaction, organic amines, for example, triethylamine and diisopropylamine are suitably used for the base.

Explanation on Synthetic Scheme B

The compound of formula (IX) can be converted into the compound of formula (III) according to, for example, F. M. Hauser et. al., J. Org. Chem., 42, 4155 (1977) described above in which the conversion of a part of the compounds is described, or a revised method thereof.

To be typical, a base (for example, diisopropylamine and diethylamine) is allowed to coexist with organic lithium (for example, t-butyllithium, n-butyllithium and the like) in an inert solvent (for example, tetrahydrofuran (THF), dimethylformamide (DMF) and dimethylsulfoxide (DMSO)) to react the compound of formula (IX) with di-lower alkyl carbonate (for example, dimethyl carbonate). Usually, this reaction can be carried out by stirring at 0 to -80° C., preferably -70 to -75° C. for one hour. Water is added to the reaction solution to further continue the reaction at a room temperature (20 to 30° C.) while stirring, whereby the intended homophthalic acid derivative is formed.

The use proportions of the respective raw materials can suitably be selected considering a profitability of the compounds used. Usually, di-lower alkyl carbonate can be used in an amount of equimole or twice mole based on the compound of formula (IX). The preferred use proportions of the other raw materials shall be able to be selected in the respective cases with reference to Production Example 1 which shall be described later.

The compound of formula (111-2) thus formed can be separated from the reaction mixture by making use of an extraction method using an organic solvent such as ethyl acetate or, if necessary, a chromatography using silica gel.

The reaction of the compound of formula (111-2) with the compound of formula (IV) can be completed by stirring them in an inert solvent (for example, dichloromethane, chloroform and the like) at 0 to 40° C., preferably a room temperature usually for 0.5 to 3 hours, preferably 2 to 3 hours in the presence of a base (for example, triethylamine, diisopropylethylamine, pyridine and the like). The preferred use proportions of the respective reactants used in the reaction described above can be settled as well with reference to the production examples described later. The respective protecting groups of the product thus obtained can be eliminated, if necessary, by a known elimination reaction, whereby it can be converted into the intended bioactive substance of formula (I).

The o-orsellinic acid derivative of formula (IX) can be produced etherifying or, if necessary, esterifying the hydroxyl groups in the 4- and/or 6-positions of o-orsellinic acid according to a known method.

Hence, according to this method, the intended compound can be produced from readily available starting materials at a very high yield by less steps.

The compound of formula (I-1) or (I)' thus formed are subjected, if necessary, to hydrolysis of the respective protecting groups to obtain particularly a compound in which $R_2$ and $R_3$ are selectively eliminated. Such hydrolytic reaction can be carried out by a publicly known method.

In particular, when $R_2$ in formula (I-1) is a lower alkyl group, it is relatively difficult to selectively eliminate only the above lower alkyl group while allowing a $R_c$ group to remain, but the reaction can suitably be allowed to proceed according to the following method. That is, typical examples of such elimination method include, for example, a method using boron tribromide and aluminum chloride which is described in "Protective groups in Organic Chemistry", John Wiley and Sons, 1991 and a method using magnesium iodide reported relatively in recent years, which is described in Anthony G. et. al., Chem. Commun., 809 (1998).

However, the reaction is drastic in the former method, so that a little elimination of $R_c$ is caused or an unfavorable effect is exerted on the other parts in a certain case. On the other hand, the above lower alkyl group can be eliminated at a good selectivity in the latter method, but magnesium iodide used is expensive, and therefore it is not suited to production in a large quantity. Accordingly, a method which can be carried out at a lower cost has so far been expected.

The present inventors have found that when $R_2$ in formula (I-1) is a lower alkyl group, a deprotecting reaction in the 8-position proceeds quantitatively by carrying out the reaction of the compound of formula (I-1) in a suitable inert solvent (for example, THF, dioxane, acetonitrile, toluene and the like) containing alkaline metal iodide (for example, potassium iodide, sodium iodide and lithium iodide) and magnesium halide (for example, magnesium fluoride, magnesium chloride and magnesium bromide, preferably magnesium chloride) at 20 to 100° C., preferably 60 to 80° C. Subsequently, the protecting group $R_3$ is eliminated by a known hydrolytic reaction, whereby the compound of formula (I) in which $R_2$ and $R_3$ in formula (I-1) are deblocked can be obtained. Hence, according to the present invention, provided is the process for producing the compound of formula (I) including the step for selectively eliminating the lower alkyl group of the compound of formula (I-1) in which $R_2$ is a lower alkyl group. In this process, alkaline metal iodide and magnesium halide are used preferably in a range of about 1:2 to 2:1 in terms of a molar ratio, but it shall not be restricted thereto. A use proportion of magnesium halide to the compound of formula (I-1) can be 0.1 to 3 times in terms of a molar equivalent.

Included in the compound of formula (I) thus obtained are 2-(8-hydroxy-6-methoxy-1-oxo-1H-2-benzopyran-3-yl) propionic acid described in WO97/48693 and other novel compounds, and it is anticipated that the novel compounds have a biological activity which is the same as or equivalent to that of the above propionic acid, so that they shall be efficient for preventing and curing an abnormal immuno-regulating action or a disease following angiogenesis. A preparation used for preventing and curing the above disease can be prepared as well in the same manner as in the above propionic acid.

The present invention shall more specifically be explained below with reference to specific production examples, but they are intended to more specifically explain the present invention but not to restrict it.

PRODUCTION EXAMPLE 1

Production of a Compound VI Represented by the Following Formula

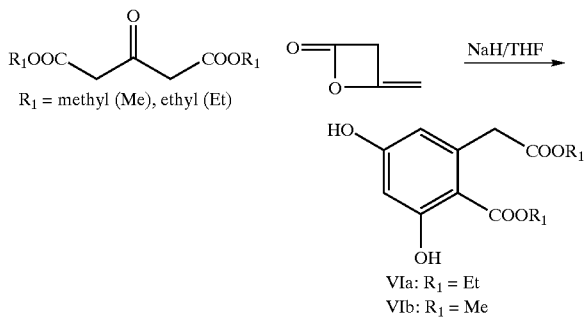

Synthesis of VIa (the Case of $R_1$=Et)

Sodium hydride (60% oil) (2.38 g, 59.3 mmol) was added to a THF 200 ml solution of diethyl acetonedicarboxylate (10.0 g, 49.4 mmol) under cooling with ice, and the solution was stirred at the same temperature for 30 minutes and at a room temperature for 30 minutes.

The reaction mixture was cooled with ice, and diketene (4.5 ml, 59.3 mmol) was dropwise added. Then, the solution was stirred at the same temperature for 2 hours, and the reaction was continued at a room temperature overnight.

The reaction mixture was quenched with 100 ml of water and adjusted to a pH 2 with 1 mol/l HCl, followed by extracting twice with 400 ml and 250 ml of ethyl acetate. The ethyl acetate layer was dried over anhydrous sodium sulfate and then concentrated to dryness to thereby obtain an oily residue. The residue was partitioned with methanol, hexane and water (150 ml:150 ml:15 ml), and the methanol layer was concentrated to dryness. The resulting residue was dissolved in 300 ml of ethyl acetate, and the ethyl acetate layer was washed sequentially with 300 ml of a 5% $NaHCO_3$ aqueous solution, 300 ml of a saturated brine, 300 ml of 0.1 mol/l HCl and 300 ml of a saturated brine, followed by drying over anhydrous sodium sulfate. The ethyl acetate layer was concentrated to dryness, and the resulting residue was refined by means of a silica gel column (400 ml, toluene; 2 1, toluene-ethyl acetate=10:1; 2.7 1) to thereby obtain 2.6 g (yield 19.6%) of the intended product.

Physico-chemical properties:
Appearance: white solid
Rf value: 0.44 (TLC: Merck Art. 5715 toluene-ethyl acetate=2:1)
FAB mass spectrum: m/z 268 (M+)
$^1$H-NMR spectrum ($CDCl_3$): δ: 1.27 (3H, t, J=7.3 Hz, $CH_3$), 1.37 (3H, t, J=7.3 Hz, $CH_3$), 3.85 (2H, s, $CH_2$), 4.17 (2H, q, J=7.3 Hz, $CH_2$), 4.35 (2H, q, J=7.3 Hz, $CH_2$), 5.93 (1H, s, OH), 6.19 (1H, d, J=2.6 Hz, CH), 6.32 (1H, d, J=2.6 Hz, CH), 11.72 (1H, s, OH)

Synthesis of VIb (the Case of $R_1$=Me)

Sodium hydride (60% oil) (0.276 g, 6.89 mmol) was added to a THF 100 ml solution of dimethyl acetonedicarboxylate (1.0 g, 5.74 mmol) under cooling with ice, and the solution was stirred at the same temperature for 30 minutes and at a room temperature for 30 minutes.

The reaction mixture was cooled with ice, and diketene (0.44 ml, 5.74 mmol) was dropwise added. Then, the solution was stirred at the same temperature for 2 hours, and the reaction was continued at a room temperature overnight.

The reaction mixture was quenched with 20 ml of water and adjusted to a pH 1 to 2 with 1 mol/l HCl, followed by extracting twice with 50 ml of ethyl acetate. The ethyl acetate layer was dried over anhydrous sodium sulfate and then concentrated to dryness to thereby obtain an oily residue. The residue was partitioned with methanol, hexane and water (30 ml:30 ml:3 ml), and the methanol layer was concentrated to dryness. The resulting residue was dissolved in 50 ml of ethyl acetate, and the ethyl acetate layer was washed in order with 50 ml of a 5% $NaHCO_3$ aqueous solution, 50 ml of a saturated brine, 50 ml of 0.1 mol/l HCl and 50 ml of a saturated brine, followed by drying over anhydrous sodium sulfate. The solvent was removed, and then the resulting residue was crystallized from chloroform-hexane to thereby obtain 0.444 g (yield 32.0%) of the intended product.

Physico-chemical properties:
Appearance: white solid
Rf value: 0.38 (TLC: Merck Art. 5715 toluene-ethyl acetate=2:1)
FAB mass spectrum: m/z 240 (M+)
$^1$H-NMR spectrum ($CDCl_3$): δ: 3.71 (3H, s, $CH_3$), 3.82 (2H, s, $CH_2$), 3.86 (3H, s, $CH_3$), 5.97 (1H, s, OH), 6.21 (1H, d, J=2.6 Hz, CH), 6.33 (1H, d, J=2.6 Hz, CH), 11.57 (1H, s, OH)

PRODUCTION EXAMPLE 2

Production of a Compound VIb Represented by the Following Formula

Dissolved in 50 ml of diethylene glycol dimethyl ether (diglyme) was 10.0 g (57.4 mmol) of dimethyl acetonedicarboxylate, and 9.7 g (228 mmol, 4 eq.) of lithium chloride was added. The solution was stirred at 130° C. for 3 hours. The reaction mixture was cooled down to a room temperature, and 50 ml of water was added thereto. Then, 17.5 ml of 2 mol/l HCl was added to acidify the solution. Added thereto was 100 ml of ethyl acetate to extract the solution, and the solution was washed each twice with 50 ml of water and 50 ml of a 5% sodium hydrogencarbonate aqueous solution and further with 50 ml of water. The resulting ethyl acetate layer was dried over anhydrous sodium sulfate, filtered and then concentrated. Added to the concentrate was 10 ml of ethyl acetate, and hexane was dropwise added, followed by stirring overnight. This was filtered out and washed with 50 ml of hexane to obtain 1.56 g (6.49 mmol, yield: 22.8%) of an intended compound.

Physico-chemical properties:
Appearance: white powder
FAB mass spectrum: m/z 240 (M+)
$^1$H-NMR spectrum (CDCl$_3$): δ: 11.57 (1H, s, OH), 6.33 (1H, d, J=2.6 Hz, CH), 6.21 (1H, d, J=2.6 Hz, CH), 5.97 (1H, s, OH), 3.86 (3H, s, CH$_3$), 3.82 (2H, s, CH$_2$), 3.71 (3H, s, CH$_3$)

PRODUCTION EXAMPLE 3
Production of a Compound V Represented by the Following Formula

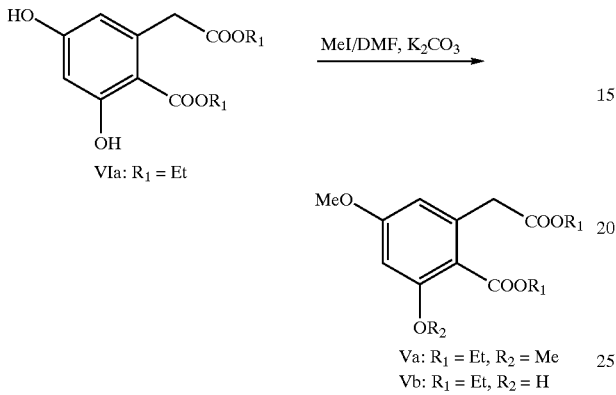

VIa: R$_1$ = Et

Va: R$_1$ = Et, R$_2$ = Me
Vb: R$_1$ = Et, R$_2$ = H

Synthesis of Va

Dissolved in 10 ml of dimethylformamide (DMF) was 1.31 g (4.89 mmol) of the dihydroxy compound VIa at a room temperature under nitrogen, and the solution was cooled down to 0° C. 2.02 g (14.7 mmol, 3.0 equivalent) of potassium carbonate and 1.33 ml (19.6 mmol, 4.0 equivalent) of methyl iodide were added to the solution, and the solution was stirred at 0° C. for 2 hours. The reaction solution was poured into water and extracted three times with ethyl acetate. The organic layers were put together and washed with a saturated brine, followed by drying over anhydrous sodium sulfate. The solvent was distilled off, and then the resulting residue was purified by a silica gel column (toluene-ethyl acetate=10:1) to thereby obtain 1.15 g (yield 79.6%) of the intended compound Va.

Compound Va (dimethoxy product): pale yellow oil
$^1$H-NMR (400 MHz, CDCl$_3$): δ6.41 (2H, s, aromatic), δ4.34 (2H, q, J=7.0 Hz, —CO$_2$CH$_2$CH$_3$), δ4.14 (2H, q, J=7.0 Hz, —CO$_2$CH$_2$CH$_3$), δ3.81 (3H, s, —OMe), δ3.80 (3H, s, —OMe), δ3.66 (2H, s, —CH$_2$—), δ1.35 (3H, t, J=7.0 Hz, —CO$_2$CH$_2$CH$_3$), δ1.25 (3H, t, J=7.0 Hz, —CO$_2$CH$_2$CH$_3$)

Synthesis of Vb

Dissolved in 30.0 ml of DMF was 3.57 g (13.3 mmol) of the dihydroxy compound VIa at a room temperature under nitrogen, and the solution was cooled down to 0° C. Added thereto were 3.67 g (26.59 mmol, 2.0 equivalent) of potassium carbonate and 2.50 ml (40.2 mmol, 3.0 equivalent) of methyl iodide, and the solution was stirred at a room temperature for one hour. The reaction solution was poured into water and extracted three times with ethyl acetate. The organic layers were put together and washed with a saturated brine, followed by drying over anhydrous sodium sulfate. The solvent was distilled off, and the resulting residue was purified by a silica gel column (silica gel: 140 ml, hexane-ethyl acetate=9:1) to thereby obtain 2.49 g (yield 66.4%) of the intended compound Vb and 0.49 g (yield 12.4%) of the dimethoxy compound Va.

Compound Vb (mono-methoxy compound): colorless needles $^1$H-NMR (400 MHz, CDCl$_3$): δ11.80 (1H, s, —OH), δ6.43 (1H, d, J=2.9 Hz, aromatic), δ6.29 (1H, d, J=2.9 Hz, aromatic), δ4.35 (2H, q, J=7.3 Hz, —CO$_2$CH$_2$CH$_3$), δ4.15 (2H, q, J=7.0 Hz, —CO$_2$CH$_2$CH$_3$), δ3.86 (2H, s, —CH$_2$—), δ3.81 (3H, s, —OMe), δ1.37 (3H, t, J=7.3 Hz, —CO$_2$CH$_2$CH$_3$), δ1.25 (3H, t, J=7.3 Hz, —CO$_2$CH$_2$CH$_3$)
FAB-MS (NBA): m/z 283 (M+H)

PRODUCTION EXAMPLE 4
Production of a Compound III Represented by the Following Formula

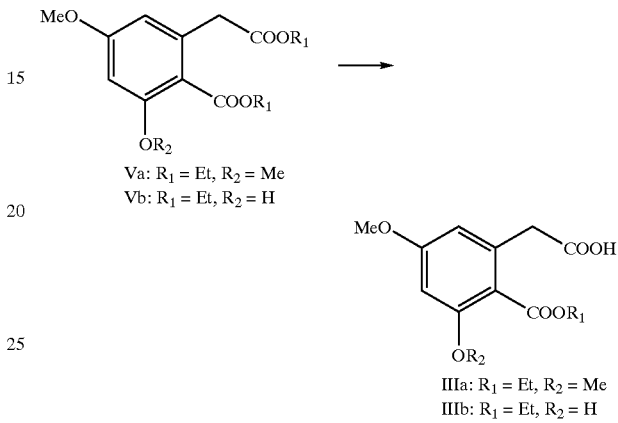

Va: R$_1$ = Et, R$_2$ = Me
Vb: R$_1$ = Et, R$_2$ = H

IIIa: R$_1$ = Et, R$_2$ = Me
IIIb: R$_1$ = Et, R$_2$ = H

Synthesis of IIIa

Dissolved in a mixed solution of 5 ml of methanol and 5 ml of acetonitrile was 1.14 g (3.85 mmol) of the dimethoxy compound Va at a room temperature under nitrogen, and 5 ml of a 1 mol/l NaOH was added thereto, followed by stirring at a room temperature for 2 hours. It was confirmed on TLC that the raw material was consumed, and the reaction solution was poured into 1 mol/l HCl. The aqueous layer was adjusted to a pH 2 and extracted three times with ethyl acetate. The organic layers were put together and washed with a saturated brine, followed by drying over anhydrous sodium sulfate. The solvent was distilled off, and then the resulting residue was left standing at a room temperature to find that crystal of the intended compound IIIa was precipitated. The crystal was filtered and washed with hexane. Methanol, chloroform and hexane were added to the filtrate, and the solution was left standing in a refrigerator overnight, whereby crystal of the intended compound IIIa was further precipitated. The crystal was filtered and washed with hexane, and then the resulting crystals were put together to obtain 0.96 g (yield 93.9%) of the intended compound IIIa.

Compound IIIa: needles
$^1$H-NMR (400 MHz, CDCl$_3$): δ6.48 (1H, d, J=2.2 Hz, aromatic), δ6.42 (1H, d, J=2.2 Hz, aromatic), δ4.41 (2H, q, J=7.3 Hz, —CO$_2$CH$_2$CH$_3$), δ3.82 (6H, s, —OMe), δ3.65 (2H, s, —CH$_2$—), δ1.38 (3H, t, J=7.3 Hz, —CO$_2$CH$_2$CH$_3$)
FAB-MS (NBA): m/z 269 (M+H)

Synthesis of IIIb

Dissolved in 10 ml of acetonitrile was 1.06 g (3.76 mmol) of the compound Vb at 0° C. under nitrogen, and a 1 mol/l NaOH was added thereto. The solution was stirred at 0° C. for 30 minutes and at a room temperature for 1.5 hour, and the reaction solution was separated into 2 layers. It was confirmed on TLC that the raw material remained, and therefore 2.0 ml of methanol was added to turn the reaction solution into a single layer, followed by further stirring at a room temperature for 2 hours. It was confirmed on TLC that the raw material was consumed, and the reaction solution was poured into 1 mol/l HCl. The aqueous layer was adjusted to a pH 2 and extracted four times with ethyl acetate (40 ml×4). The organic layers were put together and washed with a saturated brine, followed by drying over anhydrous sodium sulfate. The solvent was distilled off, and then 40 ml of n-hexane was added to the resulting residue to precipitate crystal. The crystal was filtered by vacuum to obtain 0.817 g (yield 85.6%) of the intended compound IIIb.

Compound IIIb: needles
$^1$H-NMR (400 MHz, CDCl$_3$): δ11.80 (1H, s, —OH), δ6.44 (1H, d, J=2.2 Hz, aromatic), δ6.30 (1H, d, J=2.2 Hz, aromatic), δ4.36 (2H, q, J=7.3 Hz, —CO$_2$C$\underline{H}_2$CH$_3$), δ3.90 (2H, s), δ1.37 (3H, t, J=7.3 Hz, —CO$_2$CH$_2$C$\underline{H}_3$)

FAB-MS (NBA, pos.): m/z 255 (M+H) (NBA, neg.): mlz 253 (M-H)

PRODUCTION EXAMPLE 5
Production of a Compound II Represented by the Following Formula

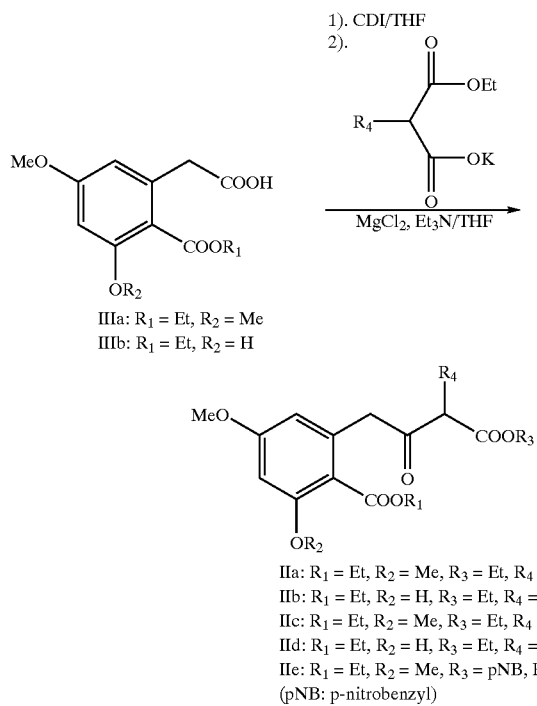

IIIa: R$_1$ = Et, R$_2$ = Me
IIIb: R$_1$ = Et, R$_2$ = H

IIa: R$_1$ = Et, R$_2$ = Me, R$_3$ = Et, R$_4$ = Me
IIb: R$_1$ = Et, R$_2$ = H, R$_3$ = Et, R$_4$ = Me
IIc: R$_1$ = Et, R$_2$ = Me, R$_3$ = Et, R$_4$ = H
IId: R$_1$ = Et, R$_2$ = H, R$_3$ = Et, R$_4$ = H
IIe: R$_1$ = Et, R$_2$ = Me, R$_3$ = pNB, R$_4$ = H
(pNB: p-nitrobenzyl)

IIa: Synthesis of R$_1$=Et, R$_2$=Me, R$_3$=Et, R$_4$=Me
Dissolved in 1.0 ml of THF was 72.0 mg (0.393 mmol, 2.1 equivalent) of an ethyl methylmalonate potassium salt at a room temperature under nitrogen, and 52.0 1 μl (0.374 mmol, 2.0 equivalent) of triethylamine and 45.0 mg (0.468 mmol, 2.5 equivalent) of anhydrous magnesium chloride were added thereto, followed by stirring at a room temperature for 4 hours. This was designated as a reaction solution A. Dissolved in 0.7 ml of THF was 50.0 mg (0.187 mmol) of the dimethoxy compound IIIa at a room temperature under nitrogen, and 33.0 mg (0.205 mmol, 1.1 equivalent) of carbonyldiimidazole (CDI) was added thereto, followed by stirring at a room temperature for 1.5 hour. This was designated as a reaction solution B.

The reaction solution A was cooled down to 0° C., and the reaction solution B was dropwise added (0.3 ml of THF was further added), followed by stirring at a room temperature for 18 hours to find that the reaction solution became a white suspension and confirm on TLC that the raw material was consumed. The reaction solution was diluted with ethyl acetate (10.0 ml) and poured into a cold 0.5 mol/l HCl aqueous solution (10.0 ml) to separate the organic layer. The aqueous layer was extracted with ethyl acetate (10.0 ml×3), and then the organic layers were put together, washed sequentially with a saturated sodium bicarbonate aqueous solution (10.0 ml) and a saturated brine (10.0 ml) and dried on anhydrous sodium sulfate. Then, the solvent was distilled off to obtain 38.3 mg (yield 56.3%) of the intended compound.

Compound IIa: needles
$^1$H-NMR (400 MHz, CDCl$_3$): δ6.48 (1H, d, J=2.2 Hz, aromatic), δ6.32 (1H, d, J=2.2 Hz, aromatic), δ4.32 (2H, d, J=7.3 Hz, —CO$_2$C$\underline{H}_2$CH$_3$), δ4.18 (2H, q, J=7.0 Hz, —CO$_2$C$\underline{H}_2$CH$_3$), δ3.91 (1H, d, J=15.4 Hz, —C$\underline{H}_2$—), δ3.87 (1H, d, J=15.4 Hz, —C$\underline{H}_2$—), δ3.81(3H, s, —OMe), δ3.80 (3H, s, —OMe), δ3.67 (1H, q, J=7.0 Hz, —C$\underline{H}$(CH$_3$)—), δ1.34 (3H, t, J=7.3 Hz, —CO$_2$CH$_2$C$\underline{H}_3$), δ1.32 (3H, d, J=7.3 Hz, —CH(C$\underline{H}_3$)), δ1.27 (3H, t, J=7.3 Hz, —CO$_2$CH$_2$C$\underline{H}_3$)

FAB-MS (NBA): m/z 353 (M+H)

Compound IIb: synthesis of R$_1$=Et, R$_2$=H, R$_3$=Et, R$_4$=Me
Dissolved in 1.0 ml of THF was 109.0 mg (0.591 mmol, 3.0 equivalent) of an ethyl methylmalonate potassium salt at a room temperature under nitrogen, and 82.0 μl (0.591 mmol, 3.0 equivalent) of triethylamine and 67.0 mg (0.690 mmol, 3.5 equivalent) of anhydrous magnesium chloride were added thereto, followed by stirring at a room temperature for 3 hours. This was designated as a reaction solution A.

Dissolved in 0.7 ml of THF was 50.0 mg (0.197 mmol) of the compound IIIb at a room temperature under nitrogen, and 73.5 mg (0.453 mmol, 2.3 equivalent) of CDI was added thereto, followed by stirring at a room temperature for 1.5 hour. This was designated as a reaction solution B.

The reaction solution A was cooled down to 0° C., and the reaction solution B was dropwise added (0.3 ml of THF was further added), followed by stirring at a room temperature for 17 hours and 70° C. for 13 hours to find that the reaction solution became a pale yellowish white suspension. The reaction solution was diluted with ethyl acetate (10.0 ml) and poured into 0.5 mol/l HCl (10.0 ml) to separate the organic layer. The aqueous layer was extracted three times with ethyl acetate (10.0 ml×3), and then the organic layers were put together, washed sequentially with a saturated sodium bicarbonate aqueous solution (10.0 ml) and a saturated brine (10.0 ml) and dried on anhydrous sodium sulfate. Then, the solvent was distilled off to obtain 40.9 mg of a residue. The residue was purified by means of PTLC (hexane:ethyl acetate=3:2) to obtain 18.0 mg (yield 28.2%) of the intended compound IIb.

IIb: white powder
$^1$H-NMR (400 MHz, CDCl$_3$): δ11.04 (1H, s, —OH), δ6.49 (1H, d, J=2.2 Hz, aromatic), δ6.37 (1H, d, J=2.2 Hz, aromatic), δ4.20 (4H, q, J=7.0 Hz, —CO$_2$C$\underline{H}_2$CH$_3$), δ3.87 (3H, s, —OMe), δ3.81 (2H, s, —C$\underline{H}_2$—), δ3.59 (1H, q, J=7.2 Hz, —C$\underline{H}$(CH$_3$)—), δ1.54 (3H, d, J=7.2 Hz, —CH(C$\underline{H}_3$)—), δ1.27 (6H, t, J=7.0 Hz, —CO$_2$CH$_2$C$\underline{H}_3$)

FAB-MS (NBA): m/z 339 (M+H)
IIc: Synthesis of R$_1$=Et, R$_2$=Me, R$_3$=Et, R$_4$=H
Dissolved in 5.0 ml of THF was 668.0 mg (3.93 mmol, 2.1 equivalent) of an ethyl malonate potassium salt at a room temperature under nitrogen, and the solution was cooled down to 0° C. Added thereto were 570.0 μl (3.74 mmol, 2.0 equivalent) of triethylamine and 445.0 mg (4.68 mmol, 2.5 equivalent) of anhydrous magnesium chloride, and the solution was stirred at a room temperature for 3.5 hours. It became difficult to stir the solution, so that 2.0 ml of THF was further added. This was designated as a reaction solution A.

Dissolved in 5.0 ml of THF was 500.0 mg (1.87 mmol) of the compound IIIa at 0° C. under nitrogen, and 333.0 mg (2.05 mmol, 1.1 equivalent) of CDI was added thereto, followed by stirring at a room temperature for one hour. This was designated as a reaction solution B.

The reaction solution A was cooled down to 0° C., and the reaction solution B was dropwise added (3.0 ml of THF was further added), followed by stirring at a room temperature for 4.5 hours to find that the reaction solution became a white suspension and confirm on TLC that the raw material was consumed. The reaction solution was diluted with ethyl acetate (40.0 ml) and poured into a cold 0.5N HCl aqueous solution (40.0 ml) to separate the organic layer. The aqueous layer was extracted three times with ethyl acetate (30.0 ml×3), and then the organic layers were put together, washed sequentially with a saturated sodium bicarbonate aqueous solution (10.0 ml) and a saturated brine (10.0 ml) and dried over anhydrous sodium sulfate. Then, the solvent was distilled off to obtain 613.8 mg (yield 97.3%) of the intended compound.

Compound IIc: colorless oil
$^1$H-NMR (400 MHz, CDCl$_3$): δ6.42 (1H, d, J=2.2 Hz, aromatic), δ6.33 (1H, d, J=2.2 Hz, aromatic), δ4.33 (2H, q, J=7.0 Hz, —CO$_2$CH$_2$CH$_3$), δ4.18 (2H, q, J=7.0 Hz, —CO$_2$CH$_2$CH$_3$), δ3.82 (3H, s, —OMe), δ3.81 (3H, s, —OMe), δ3.80 (2H, s, —CH$_2$—), δ3.49 (2H, s, —CH$_2$—), δ1.34 (3H, t, J=7.0 Hz, —CO$_2$CH$_2$CH$_3$), δ1.27 (3H, t, J=7.0 Hz, —CO$_2$CH$_2$CH$_3$)
FAB-MS (NBA): m/z 338 [M+]

IId: Synthesis of R$_1$=Et, R$_2$=H, R$_3$ Et, R$_4$=H

Dissolved in 7.0 ml of THF was 1005.0 mg (5.91 mmol, 3.0 equivalent) of an ethyl malonate potassium salt at a room temperature under nitrogen, and 823.0 μl (5.91 mmol, 3.0 equivalent) of triethylamine and 656.0 mg (6.90 mmol, 3.5 equivalent) of anhydrous magnesium chloride were added thereto, followed by stirring at a room temperature for 3 hours. This was designated as a reaction solution A.

Dissolved in 5.0 ml of THF was 500.0 mg (1.97 mmol) of the compound IIIb at a room temperature under nitrogen, and 670.0 mg (4.13 mmol, 2.1 equivalent) of CDI was added thereto, followed by stirring at a room temperature for one hour. This was designated as a reaction solution B.

The reaction solution A was cooled down to 0° C., and the reaction solution B was dropwise added (3.0 ml of THF was further added), followed by stirring at a room temperature for 48 hours to find that the reaction solution became a pale yellowish white suspension. The reaction solution was diluted with ethyl acetate (40.0 ml) and poured into a 0.5 mol/l HCl aqueous solution (30.0 ml) to separate the organic layer. The aqueous layer was extracted three times with ethyl acetate (30.0 ml×3), and then the organic layers were put together, washed in order with a saturated sodium bicarbonate aqueous solution (10.0 ml) and a saturated brine (10.0 ml) and dried over anhydrous sodium sulfate. Then, the solvent was distilled off to obtain 791 mg of a residue. The residue was purified by means of a silica gel column (silica gel 15 g, hexane:ethyl acetate=3:2→2:1→1:1) to obtain 196.1 mg (yield 30.7%) of the intended compound IId.

IId: white powder
$^1$H-NMR (400 MHz, CDCl$_3$): δ11.72 (1H, s, —OH), δ6.44 (1H, d, J=2.9 Hz, aromatic), δ6.27 (1H, d, J=2.9 Hz, aromatic), δ4.38 (2H, q, J=7.3 Hz, —CO$_2$CH$_2$CH$_3$), δ4.19 (2H, q, J=7.3 Hz, —CO$_2$CH$_2$CH$_3$), δ4.02 (2H, s, —CH$_2$—), δ3.82 (3H, s, —OMe), δ3.44 (2H, s, —CH$_2$—), δ1.36 (3H, t, J=7.3 Hz, —CO$_2$CH$_2$CH$_3$), δ1.27 (3H, t, J=7.3 Hz, —CO$_2$CH$_2$CH$_3$)
FAB-MS (NBA): m/z 325 (M+H)

IIe: Synthesis of R$_1$=Et, R$_2$=Me, R$_3$=pNB, R$_4$=H

Dissolved in 1.0 ml of THF was 50.0 mg (0.187 mmol) of the compound IIIa at 0° C. under nitrogen, and 33.0 mg (0.205 mmol, 1.1 equivalent) of CDI was added thereto, followed by stirring at a room temperature for one hour. This was designated as a reaction solution A.

Dissolved in DMF was 181.0 mg (0.337 mmol, 1.8 equivalent) of a p-nitrobenzyl malonate magnesium salt dihydrate, and then the solvent was distilled off under reduced pressure (30 to 40° C., 2 to 10 mm Hg) to obtain an anhydride thereof. This was dissolved in 1.0 ml of THF and dropwise added to the reaction solution A cooled down to 0° C., followed by stirring at a room temperature for 16 hours to find that the reaction solution became a white suspension and confirm on TLC that the raw material was consumed. The reaction solution was diluted with ethyl acetate, washed in order with cold 0.5M hydrochloric acid, a saturated sodium bicarbonate aqueous solution and a saturated brine and dried over anhydrous sodium sulfate. Then, the solvent was distilled off to obtain a residue. The residue was purified by means of PTLC (hexane:ethyl acetate=2:1,×2) to obtain 38.4 mg (yield 46.3%) of the intended compound IIe.

IIe: colorless needles
$^1$H-NMR (400 MHz, CDCl$_3$): δ8.21 (2H, d, J=8.1 Hz, m-pNB), δ7.52 (1H, d, J=8.1 Hz, o-pNB), δ6.42 (1H, d, J=2.2 Hz, aromatic), δ6.31 (1H, d, J=2.2 Hz, aromatic), δ5.25 (2H, s, —CO$_2$CH$_2$-pNB), δ4.31 (2H, q, J=7.0 Hz, —CO$_2$CH$_2$CH$_3$), δ3.82 (3H, s, —OMe), δ3.80 (3H, s, —OMe), δ3.78 (2H, s, —CH$_2$—), δ3.61 (2H, s, —CH$_2$—), δ1.32 (3H, t, J=7.0 Hz, —CO$_2$CH$_2$CH$_3$)
FAB-MS (NBA): m/z 446 (M+H)

PRODUCTION EXAMPLE 6

Production of a Compound I Represented by the Following Formula

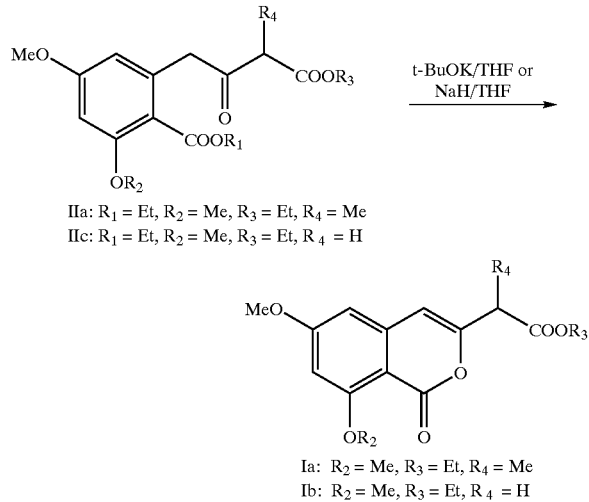

IIa: R$_1$ = Et, R$_2$ = Me, R$_3$ = Et, R$_4$ = Me
IIc: R$_1$ = Et, R$_2$ = Me, R$_3$ = Et, R$_4$ = H

Ia: R$_2$ = Me, R$_3$ = Et, R$_4$ = Me
Ib: R$_2$ = Me, R$_3$ = Et, R$_4$ = H

Ia: Synthesis of R$_2$=Me, R$_3$=Et, R$_4$=Me

Dissolved in 10.0 ml of THF was 300.0 mg (0.85 mmol) of the raw material IIa at a room temperature under nitrogen, and 120.0 mg (1.02 mmol, 1.2 equivalent) of potassium t-butoxide was added thereto, followed by stirring at a room temperature for 1.5 hour to confirm on TLC that the raw material was consumed. The reaction solution was diluted with ethyl acetate (50.0 ml) and poured into 1 mol/l HCl (30.0 ml) to separate the organic layer. The aqueous layer was extracted three times with ethyl acetate (50.0 ml×3), and then the organic layers were put together, washed with a saturated brine (30.0 ml) and dried over anhydrous sodium sulfate. Then, the solvent was distilled off to obtain 286.0 mg of a residue. The residue was purified by means of a silica gel column (silica gel 15 g, hexane:ethyl acetate=2: 1) to obtain 171.4 mg (yield 65.7%) of the intended compound Ia.

Compound Ia: pale yellow oil $^1$H-NMR (400 MHz, CDCl$_3$): δ6.46 (1H, d, J=2.2 Hz; aromatic), δ6.38 (1H, d, J=2.2 Hz, aromatic), δ6.25 (1H, s, olefin), δ4.19 (2H, q, J=7.0 Hz, —CO$_2$CH$_2$CH$_3$), δ3.96 (3H, s —OMe), δ3.89 (3H, s, —OMe), δ3.57 (1H, q, J=7.3 Hz, —CH(CH$_3$)—), δ1.53 (3H, d, J=7.3 Hz, —CH(CH$_3$)—), δ1.26 (3H, t, J=7.0 Hz, —CO$_2$CH$_2$CH$_3$)

FAB-MS (NBA): m/z 307 (M+H)

Ib: Synthesis of R$_2$=Me, R$_3$=Et, R$_4$=H

Dissolved in 1.0 ml of toluene was 50.0 mg (0.148 mmol) of the raw material IIc at a room temperature under nitrogen, and 6.0 mg (0.150 mmol, 1.0 equivalent) of sodium hydride (60% oil) and 1.4 μl (0.015 mmol, 0.1 equivalent) of tert-butanol were added thereto, followed by stirring at a room temperature for 30 minutes and 80° C. for 3 hours. It was confirmed on TLC that the raw material remained, and therefore 9.0 mg (0.225 mmol, 1.5 equivalent) of sodium hydride (60% oil) was further added at a room temperature, followed by further stirring at 80° C. for 14 hours. The reaction solution was diluted with ethyl acetate (20.0 ml) and poured into a 0.1 mol/l HCl aqueous solution (20.0 ml) to separate the organic layer. The aqueous layer was extracted three times with ethyl acetate (30.0 ml×3), and then the organic layers were put together, washed in order with a saturated sodium bicarbonate aqueous solution (10 ml) and a saturated brine (10 ml) and dried over anhydrous sodium sulfate. Then, the solvent was distilled off to obtain 48.5 mg of a residue. The residue was purified by means of PTLC (hexane:ethyl acetate=2:1) to obtain 1.5 mg (yield 3.5%) of the intended compound Ib.

Compound Ib: white powder $^1$H-NMR (400 MHz, CDCl$_3$): δ6.47 (1H, d, J=2.2 Hz, aromatic), δ6.36 (1H, d, J=2.2 Hz, aromatic), δ6.30 (1H, s, olefin), δ4.20 (2H, q, J=7.3 Hz, —CO$_2$CH$_2$CH$_3$), δ3.97 (3H, s, —OMe), δ3.96 (3H, s, —OMe), δ3.50 (2H, s, —CH$_2$—), δ1.28 (3H, t, J=7.3 Hz, —CO$_2$CH$_2$CH$_3$)

FAB-MS (NBA): m/z 293 (M+H)

PRODUCTION EXAMPLE 7
Production of a Compound Ia by One Pot Reaction

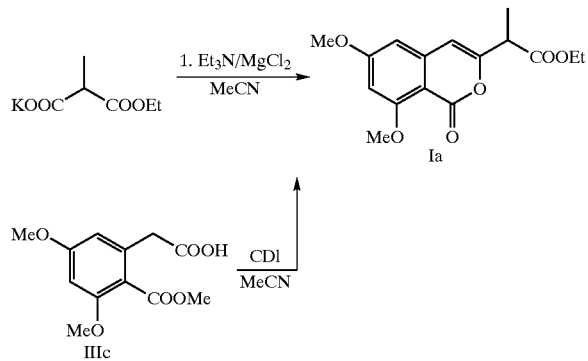

Added to an ethyl methylmalonate potassium salt (12.2 g, 66 mmol) was 135 ml of anhydrous acetonitrile, and then triethylamine (8.8 ml, 63 mmol) and anhydrous magnesium chloride (7.5 g, 79 mmol) were added. After one hour, the compound IIIc (8.0 g, 31 mmol) was dissolved in 135 ml of anhydrous acetonitrile in another flask, and then 1,1'-carbonylbis-1H-imidazole (5.6 g, 35 mmol) was added thereto. After stirring at a room temperature for 2.5 hours, this solution was dropwise added to the previous solution described above. The solution was stirred at a room temperature for 16.5 hours and then further stirred for one hour under refluxing. It was left cooling to a room temperature and then cooled with ice, and 200 ml of 0.5 mol/l HCl was added thereto. This solution was concentrated under reduced pressure to distil acetonitrile off and then extracted with 160 ml of ethyl acetate. The ethyl acetate layer was washed with 50 ml of purified water and 50 ml of a 5% sodium chloride aqueous solution and dried over anhydrous sodium sulfate. After filtering and concentrating under reduced pressure, 8 ml of ethyl acetate and 16 ml of ethanol were added and stirred for 2 hours. Precipitated crystal was filtered off to obtain 6.99 g (yield 72.2%) of the intended compound Ia showing the same $^1$H-NMR spectrum as that of the compound Ia obtained in Production Example 5.

PRODUCTION EXAMPLE 8
Production of a Compound I Represented by the Following Formula

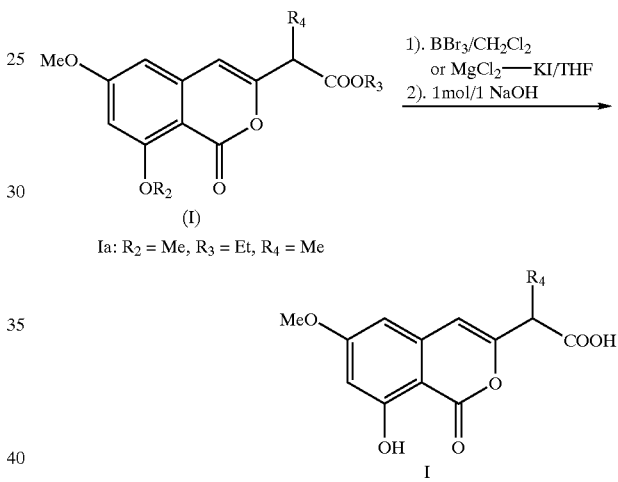

Dissolved in 1.0 ml of CH$_2$Cl$_2$ was 30.0 mg.(0.098 mmol) of the raw material Ia at 0° C. under nitrogen, and 196.0 μl (0.196 mmol, 2.0 equivalent) of boron trifluoride (1 mol/l in CH$_2$Cl$_2$ solution) was added thereto, followed by stirring at 0° C. for 1.5 hour and a room temperature for one hour to confirm on TLC that the raw material was consumed. The reaction solution was diluted with CHCl$_3$ (20.0 ml) and poured into water (10.0 ml) to separate the organic layer. The aqueous layer was extracted three times with chloroform (15.0 ml×3), and then the organic layers were put together, washed with a saturated brine (10.0 ml) and dried over anhydrous sodium sulfate. Then, the solvent was distilled off to obtain 24.8 mg (yield 86.6%) of the intended compound (8-OH substance).

(2) Another process

The compound Ia (2.45 g, 8.0 mmol), magnesium chloride (1.52 g, 16 mmol) and potassium iodide (2.62 g, 16 mmol) were suspended in 40 ml of anhydrous THF and then refluxed. After refluxing for 3 hours, the suspension was left cooling to a room temperature. Added to the reaction solution was 100 ml of ethyl acetate, and then this solution was washed with a 10% sodium thiosulfate aqueous solution. Subsequently, it was washed with purified water, 1 mol/l HCl and a saturated brine. The organic layer obtained was dried over anhydrous sodium sulfate, then filtered and concentrated to obtain 2.33 g (quant.) of the intended compound [8-OH substance (R$_3$=Et)] obtained by eliminating methyl of R$_2$ in the compound Ia.

Compound 8-OH substance (R$_3$=Et): white powder
$^1$H-NMR (400 MHz, CDCl$_3$): δ11.03 (1H, s, —OH), δ6.46 (1H, d, J=2.2 Hz, aromatic), δ6.38 (1H, d, J=2.2 Hz, aromatic), δ6.34 (1H, s, olefin), δ4.20 (2H, q, J=7.0 Hz, —CO$_2$CH$_2$CH$_3$), δ3.87 (3H, s, —OMe), δ3.59 (1H, q, J=7.3 Hz, —CH(CH$_3$)—), δ1.54 (3H, d, J=7.3 Hz, —CH(CH$_3$)—), δ1.27 (3H, t, J=7.0 Hz, —CO$_2$CH$_2$CH$_3$)

FAB-MS (NBA): m/z 293 (M+H)

Dissolved in 1.0 ml of methanol at 0° C. under nitrogen was 24.0 mg (0.082 mmol) of the 8-OH compound obtained above, and 0.5 ml of a 1 mol/l NaOH was added thereto, followed by stirring at a room temperature for 1.5 hour to confirm on TLC that the raw material was consumed. The reaction solution was diluted with ethyl acetate (10.0 ml) and poured into 1 mol/l HCl (10.0 ml), and the pH was adjusted to 2, followed by separating the organic layer. The aqueous layer was extracted three times with ethyl acetate (10.0 ml×3), and then the organic layers were put together, washed with a saturated brine (5.0 ml) and dried over anhydrous sodium sulfate. Then, the solvent was distilled off to obtain 22.1 mg (quant.) of the compound I.

Compound I: white powder
$^1$H-NMR (400 MHz, CDCl$_3$): δ10.99 (1H, s, —OH), δ6.50 (1H, d, J=2.3 Hz, aromatic), δ6.38 (1H, overlapping aromatic), δ6.38 (1H, s, olefin), δ3.87 (3H, s, —OMe), δ3.64 (1H, q, J=7.3 Hz, —CH(CH$_3$)—), δ1.57 (3H, d, J=7.3 Hz, —CH(CH$_3$)—

PRODUCTION EXAMPLE 9
Production of Homophthalic Acid Derivative (Another Process 1)

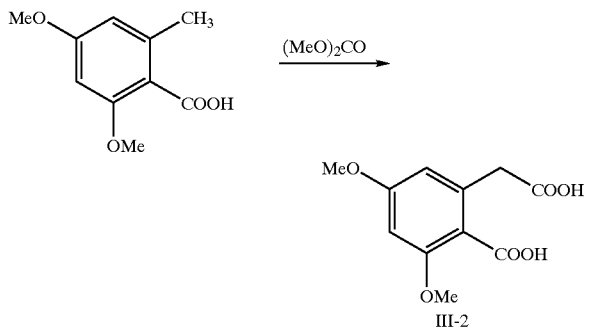

Diisopropylamine (8.08 g, 80 mmol) was dissolved in 25 ml of THF and cooled with ice. Dropwise added was 53 ml of n-butyl-lithium (hexane solution) of 1.52 mol/l while stirring. After finishing dropwise adding, the solution was stirred at the same temperature for 10 minutes and then cooled down to −70° C. A mixed solution of orsellinic acid dimethyl ether (3.92 g, 20 mmol), dimethyl carbonate (3.60 g, 40 mmol) and 25 ml of THF was dropwise added at −70° C. After finishing dropwise adding, the solution was stirred at the same temperature for 10 minutes and then a room temperature for 4 hours. Added to the reaction solution was 30 ml of purified water, and the solution was stirred overnight. The organic solvent was removed under reduced pressure, and then 100 ml of 1 mol/l HCl was added thereto. The solution was extracted with ethyl acetate (250 ml×2). The organic layer was dried over sodium sulfate, then filtered and concentrated. Added to resulting crude crystal was 25 ml of chloroform to filter the crystal off. The crystal was washed with 20 ml of chloroform to obtain 4.41 g (yield 91.9%) of the intended product.

NMR (400 MHz, CD$_3$OD): δ3.71 (s, 2H, CH$_2$), 3.82 (s, 3H, CH$_3$), 3.83 (s, 3H, CH$_3$), 6.48 (d, J=2.2 Hz, 1H, Ar), 6.54 (d, J=2.2 Hz, 1H, Ar)

FAB-MS (NBA, m/z): 240 (M+), 241 (M+H).

PRODUCTION EXAMPLE 10
Production of Isocoumarin-3-yl-acetic Acid Derivative (Another Process)

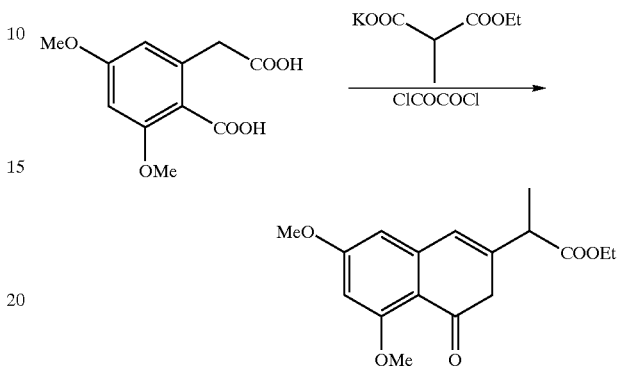

Ethyl methylmalonate (552 mg, 7.3 mmol) was suspended in 10 ml of dichloromethane under cooling with ice, and then oxalyl chloride (768 mg, 6 mmol) was added thereto. This mixed solution was dropwise added to a dichloromethane solution of 2,4-dimethoxy-homophthalic acid (240 mg) under cooling with ice. The solution was stirred at the same temperature for 30 minutes and then a room temperature overnight. Added thereto was 10 ml of purified water, and the solution was extracted with ethyl acetate (100 ml×2). The organic layer was washed with a saturated brine and then dried over sodium sulfate. After filtering and concentrating, the residue was separated and purified by means of a silica gel column chromatography (hexane-ethyl acetate=9:1 to 6:4) to obtain 128 mg (yield 41%) of the intended compound (raw material 2).

NMR (400 MHz, CDCl$_3$): δ1.26 (3H, t, J=7.0 Hz, CH$_3$), δ1.53 (3H, d, J=7.3 Hz, CH$_3$), δ3.56 (1H, q, J=7.3 Hz, CH), δ3.89 (3H, s, CH$_3$), δ3.96 (3H, s, CH$_3$), δ4.19 (2H, q, J=7.0 Hz, CH$_2$), δ6.25 (1H, s,=CH), δ6.38 (1H, d, J=2.2 Hz, Ar), δ6.46 (1H, d, J=2.2 Hz, Ar)

FAB MS (Gly, m/z): 307 (M+H).

PRODUCTION EXAMPLE 11
Production of Homophthalic Acid Derivative (Another Process 2)

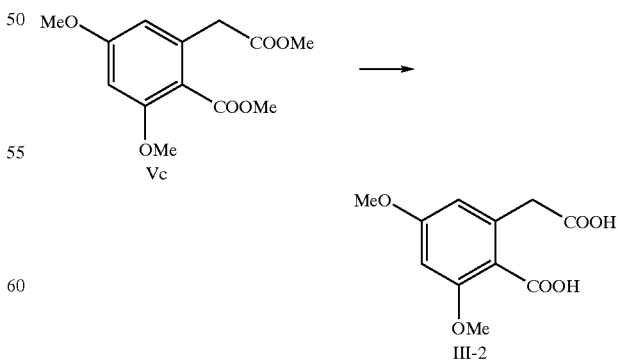

The compound Vc was dissolved in 100 ml of methanol, and then 50 ml of 2 mol/ml NaOH was added thereto at a room temperature. This reaction solution was refluxed for 6.5 hours by heating, and then 50 ml of 2 mol/ml NaOH was further added thereto. The solution was continued to be refluxed for 15 hours.

The reaction solution was allowed to come down to a room temperature, and 100 ml of water was added, followed by washing with ethyl acetate. Added to this aqueous layer was 100 ml of 2 mol/ml HCl to confirm that the pH was 1, and then it was extracted with 200 ml, 100 ml and 100 ml of ethyl acetate. These organic layers were put together and washed with 200 ml of water. The organic layer was dried over $Na_2SO_4$, filtered and concentrated. Resulting crude crystal was suspended in 100 ml of hexane, and 50 ml of ethyl acetate was added thereto, followed by stirring for 30 minutes. This was filtered and washed with 100 ml of a hexane: ethyl acetate=3:1 solution to obtain 7.37 g of crystal.

This crystal showed the same NMR spectrum as that of the homophthalic acid derivative obtained in Production Example 9.

PRODUCTION EXAMPLE 12

Production of a Compound Vc Represented by the Following Formula

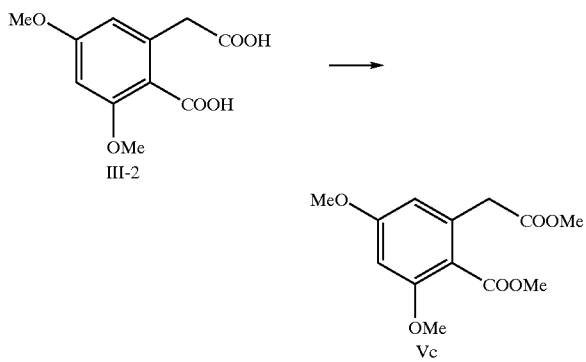

Under nitrogen, to the dicarboxylic acid (III-2) (20 mg, 0.083 mmol) in 1 ml of DMF was added potassium carbonate (34.6 mg, 3 eq., 0.25 mmol) and stirred for 30 minutes and then the reaction mixture was cooled to 0° C. The methyl iodide (15.6 μl, 3 eq., 0.25 mmol) was added to the reaction mixture at 0° C. The mixture was stirred at 0° C. for 30 minutes, and then was stirred at room temperature for 4 hours. The reaction mixture was confirm on TLC that the raw material was consumed. The mixture was poured into $H_2O$ (30 ml) and extracted twice with toluene (30 ml×2). The organic layer was washed sequentially with $H_2O$ (10 ml), 5% NaCl (10 ml) and dried over anhydrous sodium sulfate. After filtrated, the solvent was dried up under reduced pressure to obtain 22.3 mg (quant.) of an intended compound (Vc).

Vc: white amorphas $^1$H-NMR (400 MHz, $CDCl_3$): δ6.41 (1H, d, J=2.2Hz, aromatic), δ6.40 (1H, d, J=2.2 Hz, aromatic), δ3.86 (3H, s, —OMe), δ3.82 (3H, s, —OMe), δ3.81 (3H, s, —OMe), δ3.68 (3H, s, —OMe), δ3.67 (2H, s, —$CH_2$—), FAB-MS (NBA): m/z 269 ($M^+$+1)

What is claimed is:

1. A process for producing an isocoumarin-3-yl-acetic acid derivative represented by the following formula (I):

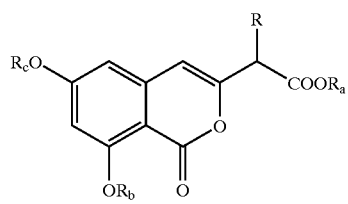

(wherein R represents a hydrogen atom, a non-substituted or substituted alkyl group, a non-substituted or substituted alkenyl group, a non-substituted or substituted alkynyl group, a non-substituted or substituted alkoxyl group, a protected amino group, a hydroxyl group or a protected hydroxyl group; $R_a$ represents a hydrogen atom or a protecting group for a carboxyl group; $R_b$ represents a hydrogen atom or a protecting group for a hydroxyl group; and $R_c$ represents a non-substituted or substituted lower alkyl group), said process comprising:
reacting a homophthalic acid derivative represented by the following formula (III):

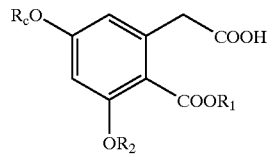

(wherein $R_c$ represents a nonsubstituted or substituted alkyl group; $R_1$ represents a hydrogen atom or a protecting group for a carboxyl group; and $R_2$ represents a hydrogen atom or a protecting group for a hydroxyl group) with a malonic acid derivative represented by the following formula (IV):

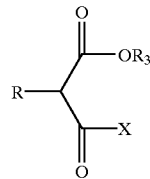

(wherein R is as defined for formula (I); $R_3$ represents a protecting group for a carboxyl group; and X represents a —OM group (wherein M is alkaline metal or alkaline earth metal), chlorine or bromine) in an inert organic solvent in the presence of a condensing agent, wherein a β-oxocarboxylic acid derivative represented by the following formula (II) in optionally formed during the above reaction:

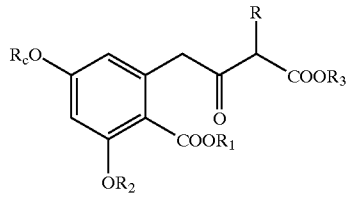

(wherein R and $R_c$ are as defined for formula (I), and $R_1$, $R_2$ and $R_3$ are as defined for formulas (III) and (IV)); and the protecting groups for the hydroxyl group and/or the carboxyl group are subjected to an elimination reaction, if necessary.

2. The process as described in claim 1, wherein the homophthalic acid derivative in which $R_1$ in formula (III) represents the protecting group for a carboxyl group is reacted with the malonic acid derivative in which X in formula (IV) represents the —OM group in the inert organic solvent in the presence of a base as the condensing agent.

3. The process as described in claim 1, wherein the homophthalic acid derivative in which $R_1$ in formula (III) represents a hydrogen atom is reacted with the malonic acid derivative of formula (IV) (wherein X represents chlorine or bromine atom) in the inert organic solvent in the presence of a dehydration type condensing agent or a base as the condensing agent.

4. A process for producing an isocoumarin-3-yl-acetic acid derivative represented by the following formula (I):

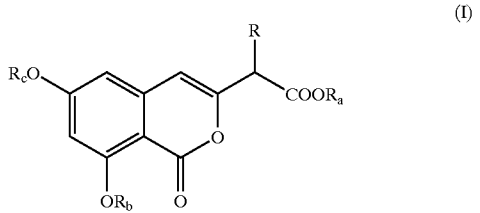

(I)

(wherein R represents a hydrogen atom, a non-substituted or substituted alkyl group, a non-substituted or substituted alkenyl group, a non-substituted or substituted alkynyl group, a non-substituted or substituted alkoxyl group, a protected amino group, a hydroxyl group or a protected hydroxyl group; $R_a$ represents a hydrogen atom or a protecting group for a carboxyl group; $R_b$ represents a hydrogen atom or a protecting group for a hydroxyl group; and $R_c$ represents a non-substituted or substituted lower alkyl group), said process comprising subjecting a β-oxocarboxylic acid derivative represented by the following formula (II) to a cyclization reaction and, if necessary, an elimination reaction of the protecting groups for a hydroxyl group and/or a carboxyl group in an inert organic solvent:

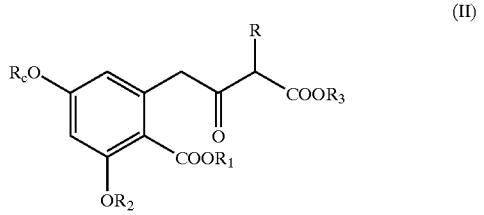

(II)

(wherein R and $R_c$ are as defined for formula (I); $R_1$ and $R_3$ represent independently a protecting group for a carboxyl group; and $R_2$ represents a protecting group for a hydroxyl group).

5. The process as described in claim 1, wherein the homophthalic acid derivative of formula (III) is produced by:

reacting an acetonedicarboxylic acid ester represented by formula (VII):

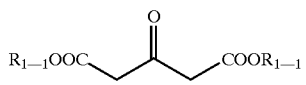

(VII)

(wherein two $R_{1-1}$'s each represent independently a protecting group for a carboxyl group) with diketene represented by formula (VIII):

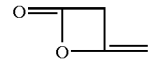

(VIII)

in an inert organic solvent to obtain a homophthalic acid diester represented by formula (VI):

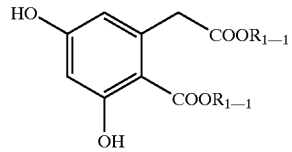

(VI)

(wherein two $R_{1-1}$'s each represent independently a protecting group for a carboxyl group), subjecting a hydroxyl group of the homophthalic acid diester of formula (IV) thus obtained to an alkylation reaction with $R_c$—I or $(R_cO)_2SO_2$ (wherein $R_c$ is as defined for formula (I) described above) in an organic solvent and, if necessary, to a reaction for protecting a non-alkylated hydroxyl group to produce a diester represented by formula (V):

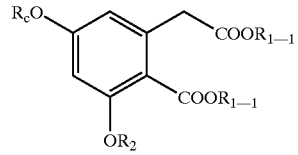

(V)

(wherein $R_c$ and $R_2$ are as defined for formula (III), and $R_{1-1}$ is as defined for formula (VII)), and then subjecting a protecting group for a hydroxyl group of the diester described above to a partial hydrolytic reaction or a full hydrolytic reaction.

6. The process as described in claim 1, wherein the homophthalic acid derivative in which $R_1$ in formula (III) is a hydrogen atom is produced by reacting an o-orsellinic acid derivative represented by formula (IX):

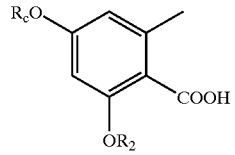

(IX)

(wherein $R_c$ and $R_2$ are as defined for formula (III)) with di-lower alkyl carbonate in an inert organic solvent in the presence of a base.

7. The process as described in claim 1, wherein in the isocoumarin-3-yl-acetic acid derivative of formula (I)

obtained by reacting the homophthalic acid derivative of formula (III) with the malonic acid derivative of formula (IV), in the case of the compound in which $R_b$ is a protecting group for a hydroxyl group and represents a lower alkyl group, said compound is subjected to a selective deblocking reaction of said $R_b$ in a suitable solvent containing an alkaline metal iodide salt and magnesium halide (provided that magnesium iodide is excluded) and then, when $R_a$ in formula (I) is a protecting group for a carboxyl group, to a deblocking reaction of said protecting group to produce the isocoumarin-3-yl-acetic acid derivative in which both $R_a$ and $R_b$ in formula (I) are hydrogen atoms.

8. The process as described in claim 5, comprising reacting the acetonedicarboxylic acid ester in which both of two $R_{1-1}$'s in formula (VII) are methyl with the diketene of formula (VIII) in an inert organic solvent to obtain the homophthalic acid derivative in which both $R_{1-1}$'s in formula (VI) are methyl, reacting said diester with a methylating agent of $CH_3I$ or $(CH_3O)_2SO_2$ in an organic solvent to produce the diester in which $R_c$, $R_2$ and $R_{1-1}$ each are methyl and a hydroxyl group is protected, subjecting said diester in which a hydroxyl group is protected to a partial hydrolytic reaction to produce the homophthalic acid derivative in which $R_c$, $R_1$ and $R_2$ in formula (III) each are methyl, reacting said homophthalic acid derivative with the malonic acid derivative in which R in formula (IV) is methyl and $R_3$ is ethyl and in which X is -OK to produce the compound in which R, $R_b$ and $R_c$ in formula (I) each are methyl and $R_a$ is ethyl, and subjecting said compound to elimination of methyl corresponding to $R_b$ in formula (I) in an inert organic solvent in the presence of alkaline metal iodide and magnesium halide (provided that magnesium iodide is excluded) and then to hydrolysis of an ester group formed by $R_3$ in formula (I) to produce the isocoumarin-3-yl-acetic acid derivative in which R and $R_c$ in formula (I) are methyl and $R_a$ and $R_b$ are hydrogen atoms.

9. The process as described in claim 1, wherein the homophthalic acid derivative of Formula (III) is produced by:

subjecting an acetonedicarboxylic acid ester represented by Formula (VII):

(VII)

(wherein two $R_{1-1}$'s each represent independently a protective group for a carboxyl group) to a cyclization dicarboxylation reaction in an inert organic solvent in the presence of a suitable inorganic salt to obtain a homophthalic acid diester represented by Formula (VI):

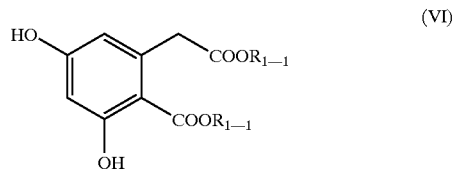

(VI)

(wherein two $R_{1-1}$'s each represent independently a protective group for a carboxyl group), subjecting a hydroxyl group of the homophthalic acid diester of Formula (VI) thus obtained to an alkylation reaction with $R_c$—I or $(R_cO)_2SO_2$ (wherein $R_c$ is synonymous with that defined in Formula (I) described above) in an organic solvent and, if necessary, to a reaction for protecting a non-alkylated hydroxyl group to produce a diester represented by Formula (V):

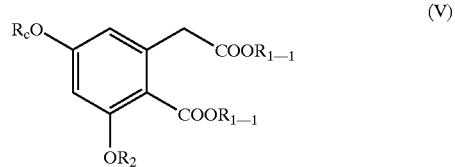

(V)

(wherein $R_c$ and $R_2$ are synonymous with those defined in Formula (III), and $R_{1-1}$ is synonymous with that defined in Formula (VII)), and then subjecting a protective group for a carboxyl group of the diester to a partial hydrolysis or a full hydrolysis.

* * * * *